US006762302B2

(12) United States Patent  
Olasz et al.

(10) Patent No.: US 6,762,302 B2  
(45) Date of Patent: Jul. 13, 2004

(54) PROCESS FOR DEHYDROGENATION OF AZAANDROSTANE COMPOUNDS

(75) Inventors: Katalin Olasz, Budapest (HU); Ágnes Pécsne Rázsó, Budapest (HU); István Barthó, Budapest (HU); Mónika Berta Hériné, Budapest (HU); Tamás Dávényi, Budapest (HU); Gábor Hantos, Budapest (HU)

(73) Assignee: Gedeon Richter, Ltd. (HU)

( * ) Notice: Subject to any disclaimer, the term of this patent is extended or adjusted under 35 U.S.C. 154(b) by 0 days.

(21) Appl. No.: 10/429,699

(22) Filed: May 6, 2003

(65) Prior Publication Data

US 2003/0215902 A1 Nov. 20, 2003

(30) Foreign Application Priority Data

May 10, 2002 (HU) .............................. 0201584

(51) Int. Cl.[7] ..................... C07D 221/18; C07D 221/02
(52) U.S. Cl. ............................. 546/77; 546/61
(58) Field of Search .................... 546/77, 61

(56) References Cited

U.S. PATENT DOCUMENTS

| | | | |
|---|---|---|---|
| 2,902,411 | A | 9/1959 | Murray et al. |
| 4,528,271 | A | 7/1985 | Cserey Pechány et al. |
| 4,749,649 | A | 6/1988 | Evans et al. |
| 5,225,335 | A | 7/1993 | Kominek et al. |
| 5,674,718 | A | 10/1997 | Michel-Briand et al. |

FOREIGN PATENT DOCUMENTS

| | | |
|---|---|---|
| CA | 2271974 | 11/2000 |
| EP | 0 155 096 A2 | 9/1985 |
| EP | 0 298 652 A2 | 1/1989 |
| EP | 0 428 366 A2 | 5/1991 |
| EP | 0 473 226 A2 | 3/1992 |
| EP | 0 655 459 A2 | 5/1995 |
| EP | 0 821 058 A2 | 1/1998 |
| EP | 0 786 011 B1 | 4/2000 |
| GB | 1318917 | 5/1973 |
| JP | 62-96084 A | 5/1987 |
| JP | 3-49684 A | 3/1991 |
| JP | 10-84954 A | 4/1998 |
| JP | 2001-352974 A | 12/2001 |
| JP | 2003-144146 A | 5/2003 |
| RU | 2 039 824 C1 | 7/1995 |
| WO | WO 88/07092 A1 | 9/1988 |
| WO | WO 96/12034 A1 | 4/1996 |
| WO | 96/12034 * 4/1996 | ................. 546/77 |

OTHER PUBLICATIONS

Chesnut, R.W., et al., "Antibacterial activity of 15–azasteroids alone and in combination with antibiotics," *Steroids* 27:525–541, Holden–Day, Inc. (1976).

Doorenbos, N.J., and Bossle, P.C., "Antimicrobial properties of 4–aza–22–oxa–5α–cholestane," *Chem. Ind.* 52:1660–1661, Society of Chemical Industry (1970).

El–Hawa, M.A., et al., "67 [1]–Dehydrogenation of Cortisol with Bacteria III—Some Biochemical Aspects of 67 [1]Dehydrogenation of Cortisol with *Corynebacterium aqui,*" *Eygpt. J. Microbiol.* 28:281–287, Natl Info & Documentation Ctr (1993).

El–Refai, A–M., et al., "Enzymic oxidation and reduction of cortisol with *Bacillus cereus*," *J. Gen. Appl. Microbiol.* 22:25–33, The Microbiology Research Foundation (1976).

Fava, F., and Ciccotosto, V.F., "Effects of randomly methylated–β–cyclodextrins (RAMEB) on the bioavailability and aerobic biodegradation of polychlorinated biphenyls in three pristine, soils spiked with a transformer oil," *Appl. Microbiol. Biotechnol.* 58:393–399, Springer–Verlag (Published online: Dec. 2001).

Grunwald, J., et al., "Asymmetric Oxidoreductions Catalyzed by Alcohol Dehydrogenase in Organic Solvents," *J. Am. Chem. Soc. 108*:6732–6734, American Chemical Society (1986).

Mahmoud, W.M., et al., "Steroid Transformation with Immobilized Locally Isolated Corynebacterium equi Cells," *Egypt. J. Microbiol.* 28:301–313, Natl Info & Documentation Ctr (1994).

(List continued on next page.)

*Primary Examiner*—Charanjit S. Aulakh  
(74) *Attorney, Agent, or Firm*—Sterne, Kessler, Goldstein & Fox P.L.L.C.

(57) ABSTRACT

The invention relates to a process for the production of compounds of general formula (I), wherein $R_1$ is a —NH-tert-butyl group or a 4-methyl-piperidino group, by bioconversion of compounds of general formula (II), wherein $R_1$ is as described above, using a biocatalyst having steroid-$\Delta^1$-dehydrogenase enzyme activity, wherein the activity of the enzyme needed for the bioconversion is produced by induction.

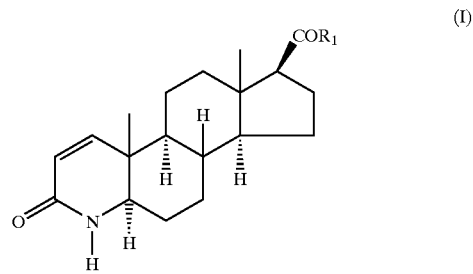

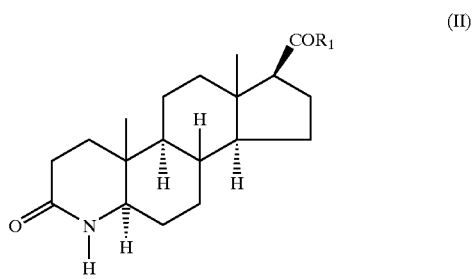

32 Claims, No Drawings

OTHER PUBLICATIONS

Marsheck, Jr., W.J., "Current Trends in the microbial transformation of steroids," in *Progress in Industrial Microbiology*, vol. 10, Hockenhull, D.J.D., ed., William Clowes & Sons, Ltd., London, Great Britain, pp. 49–103 (1971).

Mazur. R.H., and Muir, R.D., "Azasteroids. IV. Microbiological Dehydrogenation of C–Ring Azasteroids," *J. Org. Chem.* 28:2442–2443, American Chemical Society (1963).

Monsan, P., and Combes, D., "Stabilization of enzyme activity," in *The World biotech report 1984*, vol. 1, Online Publications, Ltd., Pinner, UK, pp. 379–390 (1984).

Nasseau, M., et al., "Substrate–Permeable Encapsulation of Enzymes Maintains Effective Activity, Stabilizes Against Denaturation, and Protects Against Proteolytic Degradation," *Biotechnol. Bioeng.* 75:615–618, John Wiley & Sons, Inc. (Published online: Oct. 2001).

Ryu, D.D.Y., and Lee, B.K., "An Example of Process Optimization of Enzymatic Transformation of Steroids," *Process Biochem.* 10:15–19, Wheatland Journals, Ltd. (1975).

Santaniello, E., et al., "The Biocatalytic Approach to the Preparation of Enantiomerically Pure Chiral Building Blocks," *Chem. Rev.* 92:1071–1140, American Chemical Society (1992).

Sawada, H., et al., "Mechanism of the stimulatory effect of cyclodextrins on lankacidin–producing Streptomyces," *Appl. Microbiol. Biotechnol.* 32:556–559, Springer–Verlag (1990).

Sedlaczek, L., "Biotransformations of steroids," *Crit. Rev. Biotechnol.* 7:187–236, CRC Press (1988).

Varricchio, F., et al., "Effect of Azasteroids on Gram–Positive Bacteria," *J. Bacteriol.* 93:627–635, American Society for Microbiology (1967).

Dialog File 351, Accession No. 7163814, Derwent WPI English language abstract for JP 62–96094 (Document AN1).

Dialog File 351, Accession No. 8602827, Derwent WPI English language abstract for JP 3–49684 (Document AL2).

Dialog File 351, Accession No. 10641171, Derwent WPI English language abstract for RU 2 039 824 (Document AP2).

Dialog File 351, Accession No. 11671973, Derwent WPI English language abstract for JP 10–84954, JP 2001–352974; and JP 2003–144146 (Documents AN3, AM4, AN4).

International Search Report for PCT/HU03/00036.

\* cited by examiner

PROCESS FOR DEHYDROGENATION OF AZAANDROSTANE COMPOUNDS

BACKGROUND OF THE INVENTION

1. Field of the Invention

The present invention relates to a novel process for dehydrogenation of azaandrostane compounds.

2. Related Art

The 4-azasteroids are well known specific inhibitors of the testosterone 5α-reductase enzyme. According to previously published data it is apparent that the introduction of the double bond in the C-1,2 position of the molecule is necessary for obtaining the desired effect.

There are both synthetic and biochemical methods for introducing a double bond into the C-1,2 position of 4-azasteroids.

One of the synthetic methods is the introduction of the $\Delta^1$ double bond with benzeneselenic anhydride in boiling chlorobenzene (for example, Patent No. EP 155 096).

Alternatively, dehydrogenation can be carried out with kinones (e.g. 2,3-dichloro-5,6-dicyano-benzokinone) in the presence of silylating agents (e.g., bis-trimethyl-silyl-trifluoro-acetamide) (Patent No. EP 298 652).

According to processes described in EP 428 366 and EP 655 459 the 2-halogen derivative of a steroid can be used as an intermediate to introduce the C-1,2 double bond. Patent No. CA 2 271 974 discloses a process in which the $\Delta^1$ double bond is introduced into an aza-steroid using a 2,2-dibromo-aza-steroid compound as an intermediate.

In another process, 2-halogen derivatives are prepared from the appropriate unsubstituted 4-aza compound via a trialkylsilyl-trifluoro-methanesulfonate intermediate with iodine or trimethylsilyl chloride and iodine (Patent No. EP 473 226). The desired $\Delta^1$ compound is obtained from this 2-halogen-4-aza derivative with potassium tert-butoxide in dimethylformamide solution in about 60% yield.

These synthetic methods require extremely aggressive reaction conditions that have several disadvantages. First, impurities are formed. Second, the impurities, although formed in low concentration (below 0.1%), are not characterized, and some might be toxic. In addition, some of the applied reagents are carcinogenic, flammable, demand completely dry circumstances, or are highly corrosive, and therefore are environmental hazards.

In contrast, the conditions required for biochemical methods for $\Delta^1$ dehydrogenation are gentle and produce fewer and less environmentally hazardous by-products. As a consequence, the formation of toxic compounds is less likely. Moreover, instead of two synthetic steps, the transformation can be carried out in a single step.

Although the $\Delta^1$-dehydrogenation of steroids is well known in the literature (*Microbial Transformations of Steroids*, Charney, W., Herzog, H. L., Academic Press, New York, London, (1967)), there are very few examples of the microbiological introduction of a double bond into the C-1,2 position of aza-steroids, probably because of the well known antibacterial effect of aza-steroids (*J. Bacteriol.*, 93(2), 627–35 (1967); *Steroids*, 27(4), 525–41 (1976); *Chem. Ind.*, 52, 1660–1 (1970)).

The microbial introduction of a $\Delta^1$ double bond into 12a-aza compounds has been accomplished with Nocardia sp. and Arthrobacter sp. strains (Mazur et al., *J. Org. Chem.*, 28(9), 2442–3 (1963)). According to Mazur et al., the conversion of 12a-aza-C-homo-1,4-pregnadiene-3,12,20-trione could be realized at 0.29 g/L concentration with a 62% yield; the conversion of 12a-aza- 17α-hydroxy-C-homo-1, 4-pregnadiene-3,12,20-trione could be realized at 0.17 g/L concentration with a 17% yield; and the conversion of 12a-aza-C-homo-5α-pregn-1-ene-3,12,20-trione could be realized at 0.29 g/L concentration with a 26% yield.

Similarly, Arthrobacter sp. and Nocardia sp. strains have been used to $\Delta^1$-dehydrogenate the 17-N-tert-butylcarbamoyl-4-azaandrostan-3-one substrate at 0.1–1.0 g/L concentration with a 20–80% yield (Patent No. EP 786 011). In this method, the $\Delta^1$-dehydrogenase enzymes of the above strains were induced by the addition of hydrocortisone, the separated biomass was suspended in a buffer (pH=6–8) saturated with organic solvent and the bioconversion was performed in the presence of menadione or phenazine methosulfate. The bioconversion was carried out in a small volume. In the only disclosed example the conversion was carried out for 3 days in a volume of 20 ml at 0.26 g/L substrate concentration with a 60% yield. However, for industrial realization, one must determine the appropriate concentration level and scale up the procedure. According to our experiments, when this procedure is scaled up, the conversion drops drastically. Therefore, a fundamental modification of this process is essential for industrial realization.

SUMMARY OF THE INVENTION

The aim of the present invention is to provide a bioconversion process that avoids the disadvantages of wholly synthetic methods while achieving industrial realization. More specifically, the invention relates to a process for the production of compounds of general formula (I), wherein $R_1$ is a —NH-tert-butyl group or a 4-methyl-piperidino group, by bioconversion of compounds of general formula (II), wherein $R_1$ is as described above, using a biocatalyst having steroid-$\Delta_1$-dehydrogenase enzyme activity, wherein the activity of the enzyme needed for the bioconversion is produced by induction.

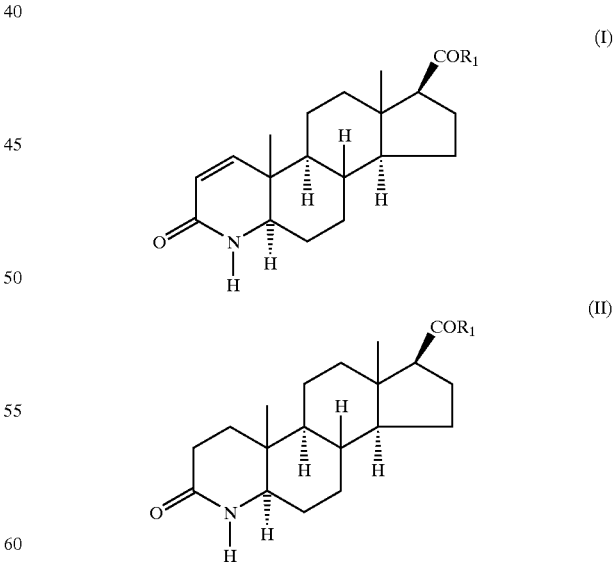

In one preferred embodiment, the present invention encompasses a method for producing a compound of formula I, comprising the steps of:

a) preparing a culture of a biocatalyst or an extract of a biocatalyst;

b) adding to the culture or extract an inducer of steroid-$\Delta^1$-dehydrogenase activity;

c) adding to the culture or extract an electron carrier, a stabilizer, and a compound of formula II; and d) incubating the culture or extract for a time sufficient for bioconversion of the compound of formula II to the compound of formula I to occur.

In another preferred embodiment, the present invention encompasses a method for producing a compound of formula I, comprising the steps of:

a) preparing a culture of a biocatalyst or an extract of a biocatalyst, wherein said culture or extract has a volume of at least about 1 L;

b) adding to the culture or extract an inducer of steroid-$\Delta^1$-dehydrogenase;

c) adding to the culture or extract an electron carrier, a stabilizer, a complexing agent or emulsifier, and a compound of formula II; and d) incubating the culture or extract for a time sufficient for bioconversion of the compound of formula II to the compound of formula I to occur.

In another preferred embodiment, the present invention encompasses a method for producing a compound of formula I, comprising the steps of:

a) preparing a culture of a biocatalyst or an extract of a biocatalyst;

b) adding to the culture or extract an inducer of steroid-$\Delta^1$-dehydrogenase;

c) adding to the culture or extract an electron carrier at a concentration of about 0.05 to about 3.5 g/L and a stabilizer at a concentration of about 0.01 to about 0.1 g/L and a compound of formula II; and d) incubating the culture or extract for a time sufficient for bioconversion of the compound of formula II to the compound of formula I to occur; provided that an oxygen scavenger is not added to the culture or extract.

DETAILED DESCRIPTION OF THE INVENTION

The invention relates to a process for the production of compounds of general formula (I), wherein $R_1$ is a —NH-tert-butyl group or a 4-methyl-piperidino group, by bioconversion of compounds of general formula (II), wherein $R_1$ is as described above, using a biocatalyst having steroid-$\Delta 1$-dehydrogenase enzyme activity, by inducing the activity of the enzyme, maintaining the activity of the enzyme at the necessary level by adding a stabilizer, promoting the continuous dissolution of the substrate by adding a complexing agent, and completing the conversion by adding an electron carrier.

The term bioconversion is defined as the conversion of compound (II) to compound (I) through the use of a biocatalyst such that at least a measurable amount of compound (I) is produced.

The term biocatalyst is defined as any microorganism that contains or can be induced to contain steroid-$\Delta^1$-dehydrogenase enzyme activity. Examples of biocatalysts include, but are not limited to, bacteria, fungi and animal cells. The method of the invention may be carried out with the above mentioned and known methods of preparing a biocatalyst (e.g., intact cells, cell free extracts, immobilized preparations thereof). For example, intact cells of Arthrobacter simplex can be used by incubating a submerged culture in a liquid medium containing a carbon source, preferably glucose in a concentration of 1–15 g/L, a nitrogen source, such as yeast extract in a concentration of 1–10 g/L, and inorganic salts. The culture is incubated at 25–38° C., preferably at 35° C., for 20–72 hours. A solution containing the agent(s) inducing the activity of the steroid $\Delta 1$-dehydrogenase enzyme is then added. For those skilled in the art, it will be apparent that the process of the invention can be carried out with other biocatalysts having steroid-$\Delta 1$-dehydrogenase activity, such as living or resting intact cells, cell lysate and free or immobilized preparations (J. Am. Chem. Soc., 108, 6732, (1986); Chem. Rev., 92, 1071–1140 (1992)).

The strains Arthrobacter sp. and Nocardia sp. may be used in the methods of the invention. Moreover, although azasteroids have an antibacterial effect, surprisingly we found that, in addition to the Arthrobacter sp. and Nocardia sp., strains belonging to the genera Bacillus and Mycobacterium were able to $\Delta 1$-dehydrogenate 4-azasteroids. Specific strains that may be used include, but are not limited to, Arthrobacter simplex (ATCC 6946), Bacillus subtilis (NRRL B-558), Bacillus sphaericus (ATCC 7054), Bacillus lentus (ATCC 13805), Nocardia corallina (ATCC 4275), and Mycobacterium sp. (NRRL B-3683). The production of cell free extracts of steroid-$\Delta 1$-dehydrogenase, as well as the immobilization of intact cells or cell free extracts from all of these strains is widely described in the literature (J. Am. Chem. Soc., 108, 6732, (1986); Chem. Rev., 92, 1071–1140 (1992)).

The activity of the $\Delta 1$-dehydrogenase enzyme is induced by a known method, such as the addition of hydrocortisone. Other inducers that may be used include, but are not limited to, prednisolone, prednisone, cortisone, and androsta-1,4-diene-3,17-dione. However, the activity of the enzyme decreases over the course of time due to the consumption of the coenzyme or the activity of proteolytic enzymes. Several known methods may be used to maintain the activity of the enzyme; such as chemical modification or immobilization of the enzyme, packing the enzyme into a liposome capsule, and the use of additives (sugar derivatives: polyols, esters; amino acids, proteins, dextrins, lecitin, DMSO). World Biotech. Rep., 1, 379–390 (1984); Patent No. JP 62-096084; Biotechnol. Bioengineer. 75, 615–618 (2001); Patent Nos. JP 96196330, JP 89185636, JP 86253336.

In the absence of an induction agent, the activity of the $\Delta^1$-dehydrogenase enzyme may drop. To compensate for this decrease, it is necessary to add more of the induction agent. For a bioconversion that continues for several days the induction agent must be added continuously in order to maintain the necessary concentration of induction agent.

The induction of the enzyme may be performed by any known method, such as by addition of a methanolic solution of hydrocortisone into the culture in a concentration of about 10 to about 100 mg/L. Since hydrocortisone is enzymatically degraded, its induction effect decreases continuously. Therefore, to maintain the high enzyme activity necessary for bioconversion, repeated addition of hydrocortisone (altogether 2.7 g/L) is required. The frequency of hydrocortisone administration is dependent on the rate of enzymatic breakdown of the hydrocortisone. Preferably, hydrocortisone is administered once per day.

According to a more preferred method, the induction can be performed by addition of steroids that are resistant to degradation by bacterial enzymes, such as 9α-hydroxylase, and that are substrates of the $\Delta^1$-dehydrogenase enzyme, or that already have a $\Delta^1$-double bond, in a concentration of about 10 to about 100 mg/L.

Surprisingly, we have had excellent results with the bioconversion process by, after the induction of the activity of the $\Delta^1$-dehydrogenase enzyme, adding a stabilizer to maintain the appropriate level of enzyme, adding a complexing agent to promote continuous dissolution of the substrate, and adding a known electron carrier to make the bioconversion complete.

It was found that compounds that cannot induce the activity of $\Delta^1$-dehydrogenase enzyme can stabilize the enzymes already present in the system and preserve their $\Delta^1$-dehydrogenase activity for a prolonged time without any other intervention. 5α-androstanediol or its 17-methyl derivative, 13-ethyl-gon-4-ene-3,17-dione or its acetoxy or hydroxy derivative, 9,11-dehydro-hydrocortisone or its acetate derivative, estr-4-ene-3,17-dione or its acetoxy or 11α-hydroxy derivative, and 13-ethyl-10,11α-dihydroxy-gon-4-ene-3,17-dione, which are added to stabilize the enzyme, can preserve the activity when added in a final concentration of about 10 to about 100 mg/L. The most preferred stabilizer is 13-ethyl-10,11α-dihydroxy-gon-4-ene-3,17-dione, which maintains the induction effect at 50 mg/L concentration for days with no loss of dehydrogenase activity experienced for 3–5 weeks when the culture is stored at 5–12° C.

The vast majority of steroids are poorly soluble in water. However, the addition of a steroid substrate dissolved in an organic solvent would not provide sufficient bioavailability in the bioconversion system. Thus, emulsifiers or complexing agents may be used in the method of the present invention to increase biological accessibility of the substrate in bioconversions performed in aqueous systems. An emulsifier, such as polyoxyethylene-sorbitan-monooleate (e.g., TWEEN-80) (Patent No. HU 216 874) in a concentration of about 0.5 to about 4 g/L may be used. Other emulsifiers that may be used include, but are not limited to, TEGIN® and TAGAT® (Goldschmidt Chemical Corp.). Alternatively, a complexing agent, for example, α-, β- and γ-cyclodextrins and cyclodextrin derivatives, may be used advantageously (Appl. *Microbiol. Biotechnol.*, 32, 556–559 (1990); "Cyclodextrins and their Industrial Uses" ed. D. Duchene, Editions de Sante, Paris, (1987); Appl. *Microbiol. Biotechnol.*, 58, 393–399 (2002); Patent No. RU 2 039 824). Another complexing agent that may be used is TAMOL® (BASF).

In the process of the present invention, cyclodextrin and cyclodextrin derivatives may be added to the medium in a concentration of about 1 to about 50 g/L. Methyl-β-cyclodextrin and hydroxypropyl-β-cyclodextrin are preferred. A cyclodextrin derivative is defined as a cyclodextrin modified by one or more moieties such that the modified cyclodextrin maintains the ability to act as a complexing agent. Moieties that may be used include methyl, dimethyl, random-methyl, carboxy-methyl, and succinyl.

Since the enzymatic conversion of the substrate of general formula (II) to the product of general formula (I) is an equilibrium reaction, to accomplish the conversion and to increase the reaction rate, according to the process of the invention, electron carriers are used, such as naphthoquinone, menadione, menadione bisulfite and phenazine methosulfate. Preferably, menadione bisulfite is used in a concentration of about 0.05 to about 3.5 g/L, more preferably in a concentration of at least 0.1, 0.5, 1.0, 1.5, or 2.0 g/L, even more preferably in a concentration of about 3.1 g/L. The addition can be performed in one batch or in several portions, but is preferably added in four portions. Preferably, the electron carrier is added at intervals of 18–24 hours.

Note that this element of the process of the invention is quite surprising, since by increasing the amount of the applied electron carrier by two orders of magnitude over the usual amount, the conversion rate can be increased substantially, without using further additives to remove the formed toxic oxygen species. The published preconception was that the use of larger amounts of electron carrier would cause the formation of toxic oxygen derivatives that would have to be removed by oxygen scavengers. See the process described in U.S. Pat. No. 4,749,649.

Applying any one of the three elements of this invention (stabilizer, complexing agent, electron carrier) individually results in a 10–15% increase in the bioconversion over that seen in its absence. However, the combined use of all of them surprisingly gives not a simple additive effect but a synergic effect resulting in a bioconversion of more than 90%.

While the bioconversion can be carried out in any volume, the present invention advantageously is carried out in a volume of at least 1 L, preferably at least 5 L.

The bioconversion can be carried out for a length of time sufficient for at least a measurable amount of bioconversion to occur, preferably at least 24 hours, more preferably at least 72 hours.

The activity of the induced culture can be increased by known methods, for example, by producing a high cell concentration. This can be accomplished by nutrient feeding, repeated inoculation or separation of the cells and resuspending them in a reduced volume. The cells can be resuspended in a buffer solution of pH 6–8, in a buffer solution saturated with organic solvent, or in fresh medium. According to a preferred method, the cells are separated and resuspended in a fresh medium containing the above mentioned ingredients so as to reach five to ten fold concentration. The substrate of general formula (II) is added to this culture of high activity in an ethanolic solution, in about 0.2 to about 2 g/L concentration, preferably in about 1 g/L final concentration.

The following examples are illustrative, but not limiting, of the methods of the present invention. Other suitable modifications and adaptations of the variety of conditions and parameters normally encountered in synthetic chemistry and bioconversion and which are obvious to those skilled in the art are within the spirit and scope of the invention.

The active ingredient content of the crystalline products obtained in the following examples was determined by HPLC.

The conditions of the measurement were as follows:

Column: LiChroCART 250-4, LiChrospher 100 CN (5 μm)

Eluent: tetrahydrofuran : water=30:60

Flow speed: 0.7 ml/min

Injected volume: 20 μL

Detection: UV, 210 nm

Temperature: 60° C.

EXAMPLE 1

*Arthrobacter simplex* (ATCC 6946) culture was maintained on solid medium of the following composition:

| Ingredient | g/L |
|---|---|
| Tryptic digest of casein | 10 |
| Yeast extract | 1 |
| NaCl | 5 |
| $MgSO_4 \cdot 7H_2O$ | 0.25 |
| $CaCl_2 \cdot 2H_2O$ | 0.07 |
| Agar | 20 | pH adjusted to 7.1–7.2, sterilized at 121° C. for 40 minutes

The inoculated medium was incubated at 32° C. for 4 days, then stored at 4–10° C. for another 30 days to start cultures. In order to produce vegetative cultures one agar slope was washed and transferred into 100 mL medium of the following composition, which was sterilized in a 500 mL Erlenmeyer flask:

| Ingredient | g/L |
|---|---|
| Yeast extract (Quest) | 5.4 |
| Dextrose | 3 | pH adjusted to 6.7–6.8 with 10% NaOH solution Sterilized at 121° C. for 30 minutes The culture was incubated at 32° C. for 24 hours on a rotary shaker at 200 rpm, then transferred into 5 L medium of the following composition, which was sterilized in a 9 L jar fermenter:

| Ingredient | g/L | Notice |
|---|---|---|
| Dextrose | 2 | Sterilized separately in an aqueous solution of 500 g/L, added prior to inoculation |
| Yeast extract (Quest) | 8 | |
| $NH_4Cl$ | 10.9 | |
| $(NH_4)_2SO_4$ | 0.5 | |
| $K_2HPO_4$ | 2.25 | |
| $KH_2PO_4$ | 0.75 | |
| $MgSO_4 \cdot 7 H_2O$ | 2.38 | |
| $CaCl_2 \cdot 2 H_2O$ | 0.29 | |
| Antifoam Struktol SB2020 | 0.062 | |

Sterilized at 121° C. for 40 minutes
pH adjusted after sterilization to 6.1–6.2 with 20% NaOH solution The cultivation was performed at 35° C. at 200 rpm and an air flow rate of 40 L/h. The production of $\Delta^1$-dehydrogenase enzyme was induced after 20 hours of cultivation by the addition of 500 mg of hydrocortisone dissolved in methanol. After 8 hours of induction the culture was centrifuged at 4800 rpm, the supernatant was discarded, and the approximately 100 mL cell concentrate was suspended in 500 mL fresh medium. This operation was repeated eight times giving altogether 4 L of biocatalyst.

The bioconversion was performed in the above mentioned jar fermenter at 30° C. at 250 rpm and an air flow rate of 60 L/h.

The formation of $\Delta^1$-dehyrogenase enzyme was induced for a second time by the addition of 250 mg of hydrocortisone. After 2 hours, 250 mg of 13-ethyl-10,11α-dihydroxy-gon-4-ene-3,17-dione was added in a methanolic solution.

The dissolution of the substrate was promoted by addition of 120 g of hydroxypropyl-β-cyclodextrin. 800 mg of 17β-tert-butylcarbamoyl-4-azaandrostan-3-one substrate was added in an ethanolic solution to the mixture.

After the addition of the substrate, 8 g of menadione bisulfite, an electron carrier, was added in four portions of 2 g each, after intervals of 19, 20, and 24 hours, respectively. After addition of each portion of the electron carrier the air flow rate was increased by 20% of the original one: providing dissolved oxygen levels of 21, 25, 30 and 36% of air saturation. After 72 hours of bioconversion the culture was extracted with an equivalent volume of chloroform and the organic layer was concentrated to dryness.

The obtained crude crystalline product was 1315 mg, which contained 755 mg of 17β-tert-butyl-carbamoyl-4-azaandrost-1-ene-3-one (94.4% conversion). The content of the active ingredient of the obtained crystalline product was determined by HPLC as described above.

EXAMPLE 2

The process described in Example 1 was applied, but 800 mg 4-methyl-1-[(5α:17β)-3-oxo-4-azaandrostane-17-yl]-carbonyl]-piperidine was used as substrate.

The obtained crude crystalline product was 1422 mg, which contained 488 mg of 4-methyl-1-[(5α,17β)-3-oxo-4-azaandrost-1-ene-17-yl]-carbonyl-piperidine as product (61% conversion).

EXAMPLE 3

The process described in Example 1 was applied for each of the following stabilizers: 5α-androstanediol and its 17-methyl derivative, 13-ethyl-4-gonene-3,17-dione and its acetoxy and 11α-hydroxy derivatives, 9,11-dehydro-hydrocortisone and its acetate derivative, 4-estren-3,17-dione and its acetoxy and 11α-hydroxy derivatives.

The obtained crude crystalline products (in the order of the above compounds) were: 1315, 1611, 1665, 1412, 1189, 1653, 1312, 1425, 1222, 1345 mg; which contained 611, 288, 318, 555, 297, 411, 428, 371, 387, 424 mg of 17β-tert-butyl-carbamoyl-4-azaandrost-1-ene-3-one, respectively. These correspond to 76, 36, 40, 69, 37, 51, 54, 46, 48, 53% conversion, respectively.

EXAMPLE 4

A culture of Mycobacterium sp. (NRRL B-3683) microorganism was prepared by prior art methods, then the process described in Example 1 was applied to accomplish the bioconversion.

The obtained crude crystalline product was 1616 mg, which contained 36 mg of 17β-tert-butyl-carbamoyl-4-azaandrost-1-ene-3-one (4.5% conversion).

EXAMPLE 5

A culture of *Bacillus subtilis* (NRRL B-558) microorganism was prepared by prior art methods, then the process described in Example 1 was applied to accomplish the bioconversion.

The obtained crude crystalline product was 1325 mg, which contained 14.4 mg of 17β-tert-butyl-carbamoyl-4-azaandrost-1-ene-3-one (1.8% conversion).

EXAMPLE 6

To a culture of *Arthrobacter simplex* (ATCC 6946) microorganism (80 L, optical density of 18–25), which was prepared by prior art methods, 8 g of hydrocortisone was added in a methanolic solution to accomplish the induction of $\Delta^1$-dehydrogenase enzyme.

The fermentation was performed at 35° C. with 200 rpm and an air flow rate of 960 L/h. Occasional foaming was suppressed by addition of Struktol SB2020 antifoaming agent.

A culture of 5000–8000 U/L activity was used to start the dehydrogenation of dihydrofinasteride. The induced culture was cooled to 30° C. and 80 g of dihydro-finasteride was added in 800 ml of ethanol. The pH was adjusted to 7.5–7.7 by addition of 200 g/L NaOH or 100 g/L $H_3PO_4$ solutions, while keeping the agitation and the air flow rate constant. After the completion of the conversion the culture was extracted with ethyl acetate and the product was isolated by known methods.

The obtained crude crystalline product was 166 g, which contained 6.8 g of 17β-tert-butyl-carbamoyl-4-azaandrost-1-ene-3-one (8.5% conversion).

EXAMPLE 7

The process described in Example 6 was applied, but the formation of Δ¹-dehydrogenase enzyme was stabilized in addition to the induction. The hydrocortisone, which is the most advantageous inducer of the enzyme, can be metabolized by the high cell density culture, and this can lead to the gradual inactivation of the already formed enzyme. According to our experiments this inactivation was avoided by adding, in addition to hydrocortisone, 6 g of 13-ethyl-10,11α-dihydroxy-gon-4-ene-3,17-dione, which is non-inductive by itself, in methanolic solution at the beginning of the induction.

The obtained crude crystalline product was 138 g, which contained 24.96 g of 17β-tert-butyl-carbamoyl-4-azaandrost-1-ene-3-one (31.2% conversion).

EXAMPLE 8

The process described in Example 6 was applied, but before addition of the substrate 6000 g of sterilized, 40% (w/w) 2-hydroxypropyl-beta-cyclodextrin solution was added in order to promote the dissolution of the substrate.

The obtained crude crystalline product was 177 g, which contained 13.8 g of 17β-tert-butyl-carbamoyl-4-azaandrost-1-ene-3-one (11.1% conversion).

EXAMPLE 9

The process described in Example 6 was applied, but after addition of the substrate 64 g of menadione bisulfite was added in 360 ml of sterilized water, as electron carrier.

The obtained crude crystalline product was 121 g, which contained 22.3 g of 17β-tert-butyl-carbamoyl-4-azaandrost-1-ene-3-one (17.8% conversion).

EXAMPLE 10

The process described in Example 6 was applied, but the methods described in examples 7 and 8 were also adopted.

The obtained crude crystalline product was 169 g, which contained 43.8 g of 17β-tert-butyl-carbamoyl-4-azaandrost-1-ene-3-one (35% conversion).

EXAMPLE 11

The process described in Example 6 was applied, but the methods described in examples 7 and 9 were also adopted.

The obtained crude crystalline product was 151 g, which contained 35 g of 17β-tert-butyl-carbamoyl-4-azaandrost-1-ene-3-one (28% conversion).

EXAMPLE 12

The process described in Example 6 was applied, but the methods described in Examples 8 and 9 were also adopted.

The obtained crude crystalline product was 187 g, which contained 27.5 g of 17β-tert-butyl-carbamoyl-4-azaandrost-1-ene-3-one (22% conversion).

EXAMPLE 13

The process described in Example 6 was applied, but the methods described in Examples 7, 8 and 9 were also adopted.

The obtained crude crystalline product was 154 g, which contained 64 g of 17β-tert-butyl-carbamoyl-4-azaandrost-1-ene-3-one (80% conversion).

What is claimed is:
1. A method for producing a compound of formula I

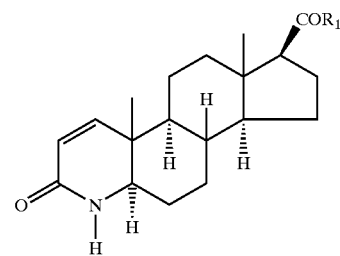

wherein $R_1$ is —NH-tert-butyl or 4-methyl-piperidino; comprising the steps of:
   a) preparing a culture of a biocatalyst or an extract of a biocatalyst;
   b) adding to the culture or extract an inducer of steroid-Δ¹-dehydrogenase activity;
   c) adding to the culture or extract an electron carrier, a stabilizer, and a compound of formula II;

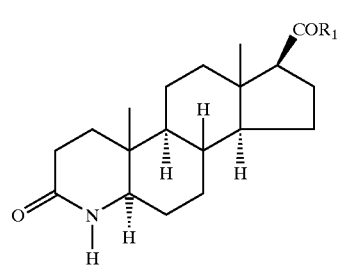

and
   d) incubating the culture or extract for a time sufficient for bioconversion of the compound of formula II to the compound of formula I to occur.

2. The method of claim 1, further comprising adding a complexing agent or emulsifier to the culture or extract prior to step (d).

3. The method of claim 1 or 2, wherein said biocatalyst is a bacteria selected from the group consisting of Arthrobacter and Nocardia.

4. The method of claim 3, wherein said bacteria is *Arthrobacter simplex*.

5. The method of claim 1 or 2, wherein said biocatalyst is a bacteria selected from the group consisting of Bacillus and Mycobacterium.

6. The method of claim 1 or 2, wherein said incubation is continued for at least about 24 hours.

7. The method of claim 1 or 2, wherein said culture or extract has a volume of at least about 1 L.

8. The method of claim 1 or 2, wherein said inducer is hydrocortisone.

9. The method of claim 8, wherein said hydrocortisone is added at a concentration of about 10 to about 100 mg/L.

10. The method of claim 1 or 2, wherein said electron carrier is selected from the group consisting of naphthoquinone, menadione, menadione bisulfite, and phenazine methosulfate.

11. The method of claim 10, wherein said electron carrier is added at a concentration of about 0.05 to about 3.5 g/L.

12. The method of claim 1 or 2, wherein said stabilizer is selected from the group consisting of 5α-androstane-diol or its 17-methyl derivative, 13-ethyl-gon-4-ene-3,17-dione or its acetoxy or hydroxy derivative, 9,11-dehydro-hydrocortisone or its acetate derivative, estr-4-en-3,17-dione or its acetoxy or hydroxy derivative, and 13-ethyl-10,11α-dihydroxy-gon-4-ene-3,17-dione.

13. The method of claim 12, wherein said stabilizer is 13-ethyl-10,11α-dihydroxy-gon-4-ene-3,17-dione.

14. The method of claim 12, wherein said stabilizer is added at a concentration of about 10 to about 100 mg/L.

15. The method of claim 1 or 2, wherein said compound of formula II is added at a concentration of about 0.2 to about 2 g/L.

16. The method of claim 2, wherein said complexing agent is a cyclodextrin or a cyclodextrin derivative selected from the group consisting of α-cyclodextrin, β-cyclodextrin, γ-cyclodextrin, methyl-β-cyclodextrin, and hydroxypropyl-β-cyclodextrin.

17. The method of claim 16, wherein said cyclodextrin or cyclodextrin derivative is added at a concentration of about 1 to about 50 g/L.

18. The method of claim 2, wherein said emulsifier is a polyoxyethylene-sorbitan-monooleate.

19. A method for producing a compound of formula I

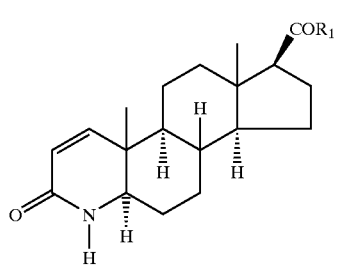

I wherein $R_1$ is —NH-tert-butyl or 4-methyl-piperidino; comprising the steps of:
  a) preparing a culture of a biocatalyst or an extract of a biocatalyst, wherein said culture or extract has a volume of at least about 1 L;
  b) adding to the culture or extract an inducer of steroid-Δ1-dehydrogenase activity;
  c) adding to the culture or extract an electron carrier, a complexing agent or emulsifier, and a compound of formula II;

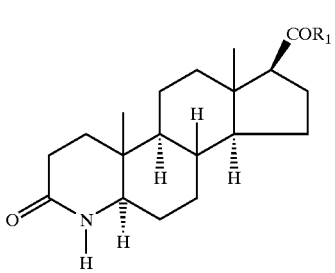

II and
  d) incubating the culture or extract for a time sufficient for bioconversion of the compound of formula II to the compound of formula I to occur.

20. The method of claim 19, wherein said biocatalyst is a bacteria selected from the group consisting of Arthrobacter and Nocardia.

21. The method of claim 20, wherein said bacteria is *Arthrobacter simplex*.

22. The method of claim 19, wherein said biocatalyst is a bacteria selected from the group consisting of Bacillus and Mycobacterium.

23. The method of claim 19, wherein said incubation is continued for at least about 24 hours.

24. The method of claim 19, wherein said inducer is hydrocortisone.

25. The method of claim 24, wherein said hydrocortisone is added at a concentration of about 10 to about 100 mg/L.

26. The method of claim 19, wherein said electron carrier is selected from the group consisting of naphthoquinone, menadione, menadione bisulfite, and phenazine methosulfate.

27. The method of claim 26, wherein said electron carrier is added at a concentration of about 0.05 to about 3.5 g/L.

28. The method of claim 19, wherein said compound of formula II is added at a concentration of about 0.2 to about 2 g/L.

29. The method of claim 19, wherein said complexing agent is a cyclodextrin or a cyclodextrin derivative selected from the group consisting of α-cyclodextrin, β-cyclodextrin, γ-cyclodextrin, methyl-β-cyclodextrin, and hydroxypropyl-β-cyclodextrin.

30. The method of claim 29, wherein said cyclodextrin or cyclodextrin derivative is added at a concentration of about 1 to about 50 g/L.

31. The method of claim 19, wherein said emulsifier is a polyoxyethylene-sorbitan-monooleate.

32. A method for producing a compound of formula I

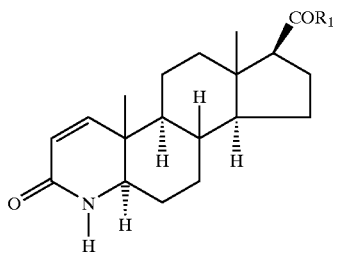

I wherein $R_1$ is —NH-tert-butyl or 4-methyl-piperidino; comprising the steps of:
  a) preparing a culture of *Arthrobacter simplex;*
  b) adding to the culture hydrocortisone as an inducer of steroid-$Δ^1$-dehydrogenase activity;
  c) adding to the culture 13-ethyl-10,11α-dihydroxy-gon-4-ene-3,17-dione as a stabilizer, menadione bisulfite as an electron carrier, hydroxypropyl-β-cyclodextrin as a complexing agent, and a compound of formula II;

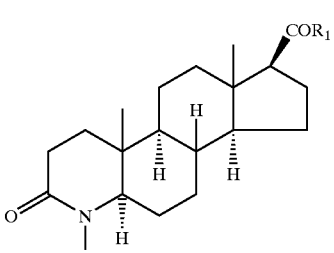

II and
  d) incubating the culture for a time sufficient for bioconversion of the compound of formula II to the compound of formula I to occur.

* * * * *